United States Patent [19]
Straihammer et al.

[11] Patent Number: 5,139,422
[45] Date of Patent: Aug. 18, 1992

[54] SLEEVE FOR A MEDICAL INSTRUMENT, PARTICULARLY A DENTAL HANDPIECE, AND THE METHOD OF MANUFACTURE

[75] Inventors: Reinhard Straihammer; Werner Schuss, both of Heppenheim, Fed. Rep. of Germany

[73] Assignee: Siemens Aktiengesellschaft, Munich, Fed. Rep. of Germany

[21] Appl. No.: 159,753

[22] Filed: Feb. 24, 1988

[30] Foreign Application Priority Data

Feb. 26, 1987 [DE] Fed. Rep. of Germany ....... 3706261

[51] Int. Cl.⁵ ............................................. A61C 1/08
[52] U.S. Cl. ................................... 433/126; 433/114; 433/116
[58] Field of Search ................. 433/126, 114, 116, 85, 433/87, 115, 124, 133; 420/420

[56] References Cited

U.S. PATENT DOCUMENTS

| | | | |
|---|---|---|---|
| 4,007,529 | 2/1977 | Fleer | 32/27 |
| 4,264,306 | 4/1981 | Leonard | 433/114 X |
| 4,278,429 | 7/1981 | Straihammer et al. | 433/126 |
| 4,299,626 | 11/1981 | Paton et al. | 420/420 |
| 4,325,696 | 4/1982 | Rosenstatter et al. | 433/126 X |
| 4,332,562 | 6/1982 | Schuss et al. | 433/126 |
| 4,655,709 | 4/1987 | Fleer | 433/126 X |
| 4,792,304 | 12/1988 | Schuss et al. | 433/126 |

FOREIGN PATENT DOCUMENTS

2029232  3/1980  United Kingdom .

OTHER PUBLICATIONS

B. C. Kellock, "Superplastic forming" *Machinery and Production Engineering*, 30 Jun. 1976, vol. 128, No. 3316, pp. 618–621.

Primary Examiner—Robert P. Swiatek
Assistant Examiner—Nicholas D. Lucchesi
Attorney, Agent, or Firm—Hill, Van Santen, Steadman & Simpson

[57] ABSTRACT

A sleeve that has the shape seen in the longitudinal direction that deviates in cross section and/or has an outside diameter that changes from a shape with a rotational symmetry to a shape with a non-rotational symmetry and has a ridge extending at least a portion of the length of the sleeve to form ledges between the ridge and adjacent curved surfaces. A method for manufacturing the sleeve includes inserting a workpiece in a die having the desired contour for the outer surface of the sleeve, heating the material and subjecting the material to internal pressure to deform the workpiece into the contour of the die to form the sleeve.

12 Claims, 2 Drawing Sheets

SLEEVE FOR A MEDICAL INSTRUMENT, PARTICULARLY A DENTAL HANDPIECE, AND THE METHOD OF MANUFACTURE

BACKGROUND OF THE INVENTION

The present invention is directed to a sleeve for a medical instrument, such as a dental instrument, said sleeve having a curvature and having both an outside shape in cross section and an outside diameter which deviate from a shape with a rotational symmetry. The invention is also directed to a method of forming the sleeve from a material suitable for super-plastic deformation.

Whether for reasons of functions or manipulations, or for the reasons of design, medical instruments, particularly instruments for dental medicine such as drilling, grinding, spraying or similar handpieces, require a shape that can deviate greatly from a cylindrical form under certain conditions. Thus, dental turbine handpieces or what are referred to as hand-and-angle pieces are usually fashioned greatly tapered toward the tool end. Over and above this, the handpieces often do not have a rotational symmetry and comprise what is referred to as a counter-bend in the gripping region. The outside contour of such a bend has been previously achieved, either in that two or more rotational symmetrical sleeves are joined to one another at the desired angle, such as disclosed by U.S. Pat. No. 4,007,529, with the two parts being connected such as by being screwed together or in that the desired bend contour has been milled out of the full form, for example out of a sleeve having a corresponding great wall thickness, such as disclosed by U.S. Pat. No. 4,332,562. This latter method of manufacture is, in fact, relatively intensive in material use, however, it has the advantage that the sleeve need not be divided into two members in the region of the location for the bend and the bend can be designed with a softer overall curvature and, thus, an overall contour of the handpiece can be more harmonically designed.

Other known methods employed in turbine handpieces for bending a cylindrical tube, which remains constant in diameter in accordance with the desired bend, is only suitable for those instruments in which the interior need not accept any parts, such as drive shafts and their bearings effected with fits or, respectively, tolerances on the inside. In addition, graduations in the outside diameter are only possible by joining tubes having different diameters or on the basis of the milling from the full form cited hereinabove.

In instruments that do not have a rotational symmetrical contour, for example in spray handles, it has been known to manufacture the grip sleeve from two halfshells, which will be formed by a longitudinal division of the sleeve. These half-shells are manufactured in accordance with a deep-drawing or stamping process. Such a sleeve produced in accordance with the deep-drawing or stamping process only allows simple contours to be provided but, by contrast, does not allow any contours having pronounced outside edges or changes in the outside surface. Added thereto is the fact that the manufacturing outlay is relatively high in order to obtain exact fitting half-shells. As a consequence of the high mold pressures, the apparatus outlay is comparatively high. Furthermore, additional calibration devices are required.

SUMMARY OF THE INVENTION

The object of the present invention is to provide a sleeve for a medical instrument which, in the longitudinal direction, can have a changing cross section and/or outside diameter, which is not necessarily rotationally symmetrical, an intermediate blank of the sleeve and to a method of producing the sleeve.

The sleeve of the species can be largely, freely designed with respect to its outside contour, namely both with respect to diameter, cross sectional shape and shaping in a longitudinal direction, in particular allowing for pronounced outside edges and is not bound to a material-intensive and apparatus-intensive type of manufacture. The sleeve of the present invention produced in accordance with this method is preferably of a material which can be subjected to a super-plastic deformation and can be manufactured in nearly any desired shape, namely with respect to diameter, cross section shape and shape in a longitudinal direction. It can be advantageous produced of two half-shells or from a rolled sheet, which was pre-bent roughly tubular. It is especially advantageous to employ a seamless drawn tube, which is of a material that is already suitable for super-plastic deformation.

The sleeve advantageously contains no guides or retaining parts for agent lines and, on the contrary, these are only component parts of separate base members of the instrument onto which the sleeve is slipped. Particularly for the manufacture of outside sleeves of the dental, motor-driven handpieces, it is advantageous to fashion a sleeve of one piece overlapping the drive. When such a hand instrument contains a plurality of sleeves lying in axial succession, then it is advantageous to fashion the sleeve blank of one piece and to separate the individual sleeves from this sleeve blank after the conclusion of the deforming process. An especially advantageous manufacture can be achieved when a plurality of such sleeve blanks containing one or more individual sleeves are manufactured from the raw initial material in an interconnecting succession of a repeating sequence. A plurality of sleeves can, thus, be simultaneously manufactured in one production process.

Other advantages and features of the invention will be readily apparent from the following description of the preferred embodiment, the drawings and claims.

BRIEF DESCRIPTION OF THE DRAWINGS

FIG. 4 is a perspective view of a sleeve blank formed in accordance with the present invention;

DESCRIPTION OF THE PREFERRED EMBODIMENTS

Figure 1:
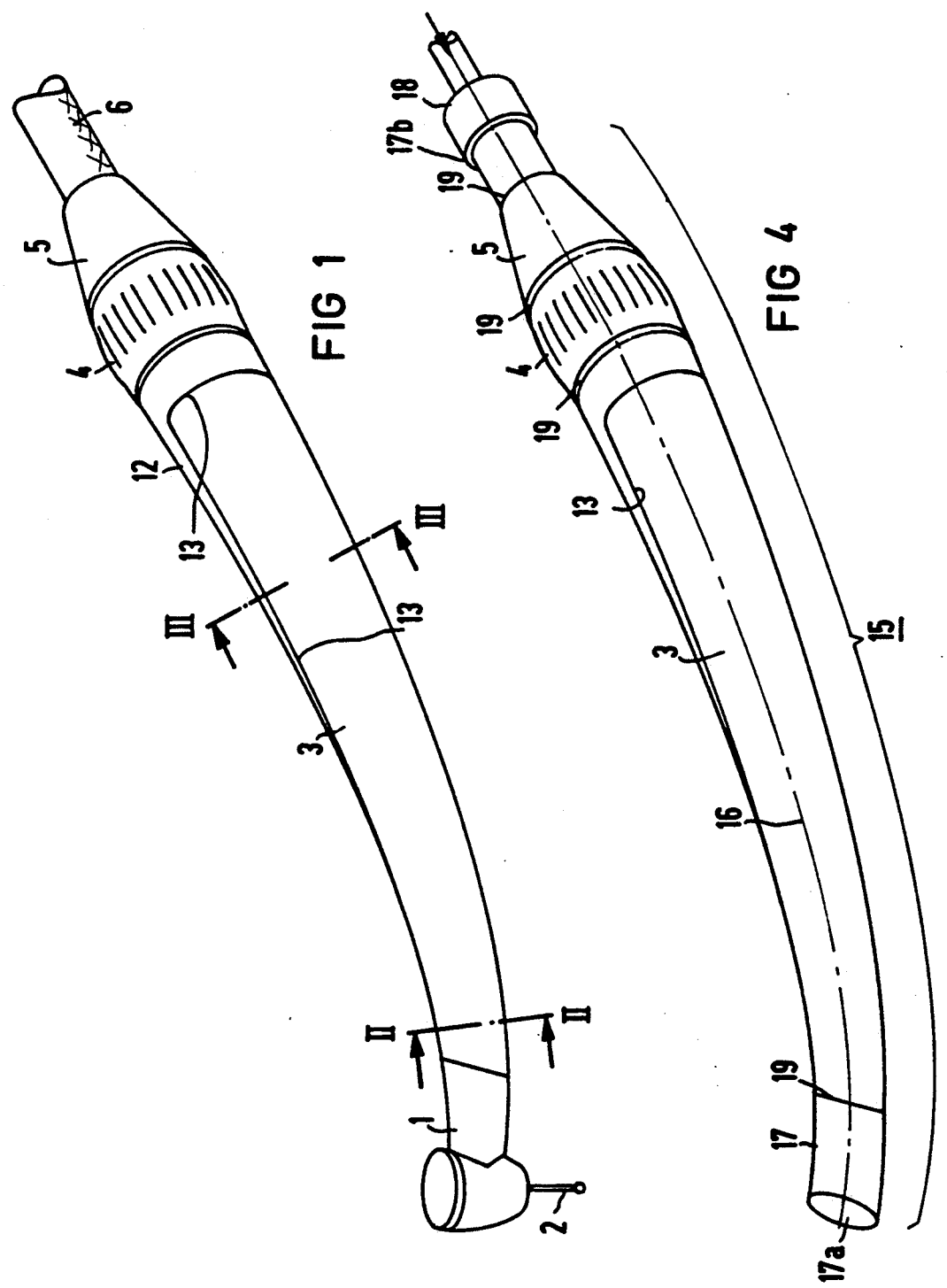
FIG. 1 is a perspective view of a complete dental instrument in accordance with the present invention.

The principles of the present invention are particularly useful when forming a sleeve for a dental handpiece instrument, illustrated in FIG. 1, which is often referred to in the technical language as a hand-andangle piece. The dental instrument is essentially composed of a head part 1, in which a tool 2 is mounted by a chuck for rotation, a grip sleeve 3, an annular sleeve or ring 4 that is part of a spray control means, and a sleeve 5 that is part of a fitting for connecting a supply hose 6 to the dental handpiece. The hand instrument involves an instrument which has a drive arrangement in the interior of the handpiece. As illustrated in the cross sectional view of FIG. 3, a drive motor 7, which may be either an electric motor or an air motor, has a drive shaft 8 which extends to the head part 1 in one or more sections in a known matter. The motor 7 is mounted in a rear part of the grip sleeve 3 in the present exemplary embodiment. A base member 9, which is illustrated as being tubular, receives the motor and is provided for the acceptance of the drive shaft sections and their bearings. Various lines, which will conduct air, water and light, are indicated at 10 and are mounted on an outer surface of the cylindrical base member 9.

Figure 2:
FIG. 2 is a cross sectional view taken along the lines II—II of FIG. 1.
Figure 3:
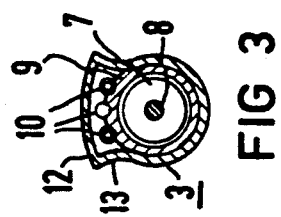
FIG. 3 is a cross sectional view taken along the lines III—III of FIG. 1.

As illustrated, the outer sleeve of the grip piece 3 has an outwardly extending ridge or saddle 12, which merges into the contour of the annular sleeve in FIG. 3. As you proceed along the sleeve 3 from the position of the cross sectional view of FIG. 3 towards the position of the cross sectional view of FIG. 2, the cross section merges from the shape illustrated in FIG. 3 to a substantially oval shape of FIG. 2, which is more circular than that of FIG. 3. Thus, the sleeve will change from both different outside diameters or dimension, as well as to different cross sectional shapes. As mentioned hereinbefore, the upper part of the sleeve, which is adjacent the connection to the supply line 6 has the ridge or saddle 12 which merges into a nearly cylindrical contour adjacent the head part 1 as well as adjacent the control sleeve 4. The transition from the ridge to the roughly cylindrical or curved contour of the gripping sleeve intentionally forms a noticeably pronounced contour edge or ledge 13 that lends the handpiece a good appearance, which is visibly noticeable to the eye.

As known, the connecting fitting sleeve 5 encompasses the actual connecting fitting, which is conventional, is not illustrated in greater detail in the Figure, and which connects the supply line for air, water and electrical power coming from the supply hose 6 into the handpiece. The inside of the spray control sleeve 4 likewise contains a member for conducting the agents through and forming the mixing chamber that is connected, first, to the connecting fitting which is covered by the sleeve 5 and, second, to a member (not shown) that is covered by the gripping sleeve 3. The spray control sleeve 4 is built to rotate relative to the sleeves 5 and 3 so that the mixing valve for the part of the air and water can be actuated with rotation of the sleeve 4. The head part 1 and the gripping sleeve 3 can be rotated together relative to the supply hose 6, to which end an appropriate rotating joint is provided. Since these parts are not the subject matter of the invention, the application has not illustrated these in greater detail, and it is noted that the rotational joints for allowing rotation can be of conventional design.

Proceeding on the basis of the gripping sleeve 3, the spray control 4 and the connection sleeve 5 are three sleeves which are separate from one another in the assembled condition, and these sleeves differ in design and are advantageously fabricated from one common sleeve blank 15 that is shown in the perspective view in FIG. 4. The sleeve blank 15 contains the gripping sleeve segment 3, the spray control sleeve segment 4 and the conical fitting sleeve segment 5. The initial material is a seamless drawn tube 17 of a material which is suitable for super-plastic deformation that is pre-bent in accordance with dot-dash 16 to form the desired bend configuration for the handpiece. A titanium alloy having the specifications of Ti, 3Al, 2.5V or Ti, A16, V4 is advantageously provided for this purpose and is, first, particularly well-suited for such deformation. In addition, it is particularly well-suited for medical applications because of its resistance to both temperature and medication.

Figure 5:
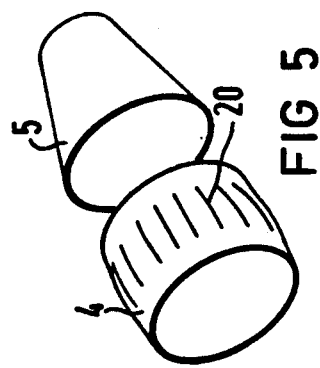
FIG. 5 is a perspective view of two sleeve segments or portions separated from the formed sleeve blank of FIG. 4.

The pre-bent, seamless drawn initial tube 17 is placed in a die corresponding to the final shape of the sleeve segments or portions 3, 4 and 5, which die is made of an extremely heat-resistant material. A tube end 17a is closed and a pressure connection 18 is connected to the other tube end 17b. Gas is then inserted into the tube to a defined pressure via the pressure connection 18 as the tube situated in the die has been heated to such a degree that it will deform under the pressure to assume the contour of the die. After deformation and cooling, the sleeve blank 15 is then trimmed to the desired shape by cutting at locations 19 to produce three sleeve segments 3, 4 and 5 in their final condition, with the sleeves 4 and 5 being best illustrated in FIG. 5. In the exemplary embodiment, the sleeve 4 has a circular cross section at both ends and has a convexity 20 in the middle provided with depressions or elevations. This is especially favorable for the actuation of the sleeve and the valve associated therewith. The connecting fitting sleeve 5 has the conical construction, as illustrated.

Figure 6:
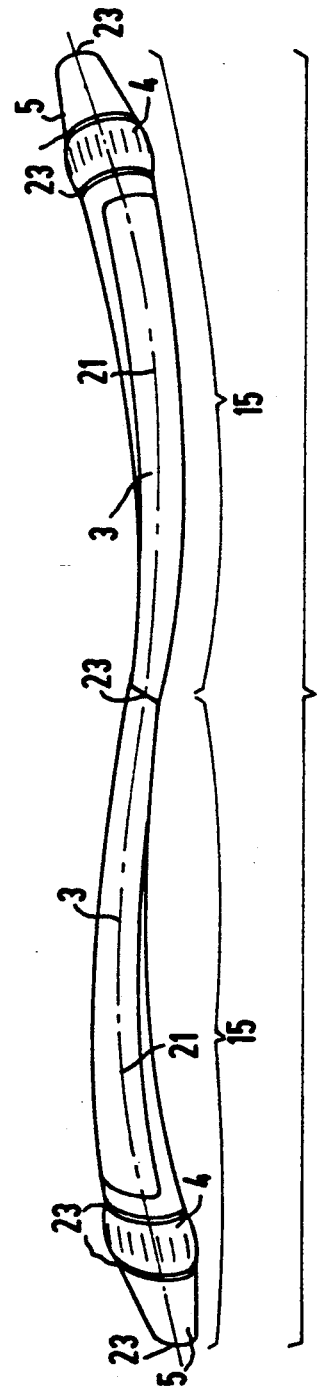
FIG. 6 is a side view of an embodiment of a sleeve blank in accordance with the present invention.

An embodiment of the blank is illustrated in FIG. 6 and has the special advantage of manufacturing a plurality of sleeve segments, which are joined one to another in a repeating sequence in one working cycle. Here, too, a tube suitable for super-plastic deformation is provided as a initial material that is pre-bent in accordance with the dot-dash line curve 21. A die, in which the tube is placed, is constructed so that a blank 22, which practically conforms to two of the sleeve blanks 15 shown in FIG. 4 will be produced in the aforementioned way, with the ends corresponding to the smallest diameter abutting each other. After parting at the locations indicated at 23, the sleeves of the two instruments, as shown in FIG. 1, are, thus, created. In that the sleeve material is pressed against the contour of the die under pressure in the plastic deformation condition, a faultless surface design that requires no after-working can be achieved in one working cycle.

With regard to the formation, the super-plastic deformation, with the above-mentioned alloys, is accomplished by heating the tube to a temperature of approximately 950° C., at which the tube becomes super-plastic so that it can be forced against the contour of the die by the application of the internal air pressure in a manner similar to blowing glass.

Although various minor modifications may be suggested by those versed in the art, it should be understood that we wish to embody within the scope of the patent granted hereon all such modifications as reasonably and properly come within the scope of our contribution to the art.

We claim:

1. A sleeve for a medical instrument, including instruments for dental medicine, said sleeve, in a longitudinal direction, having a curve and having a shape deviating in cross section along an outer dimension from a non-rotational symmetric shape towards a substantially circular cross section, said sleeve having a ridge extending for a portion of its length, said ridge forming ledges with curved surface portions of the sleeve, said sleeve being a homogeneous one-piece tubular member of a metal material being suitable for a super-plastic deformation.

2. A sleeve according to claim 1, wherein the wall thickness of the sleeve changes as the outside dimension of the sleeve changes with the thickness being greater with a smaller dimension.

3. A sleeve according to claim 1, wherein the material of the sleeve is a titanium alloy.

4. A sleeve according to claim 3, wherein the titanium alloy is Ti, 3Al, 2,5V.

5. An intermediate sleeve blank having sleeve portions for a dental instrument, said blank being a homogeneous one-piece seamless tubular member of a metal material, said sleeve portions being interconnected at their ends and including at least a first sleeve portion for a grip sleeve of the dental instrument and a second sleeve portion for covering a fitting for a connection of a supply line to the instrument, said first sleeve portion having a changing contour from a non-circular contour towards a circular contour with a ridge extending a portion of the way along the first sleeve portion and forming ledges between the ridge and curved surface portions of the first sleeve portion and said second sleeve portion having a circular cross section tapering to a smaller circular cross section.

6. An intermediate sleeve blank according to claim 5, which includes a repeating sequence of the interconnecting sleeve portions so that a plurality of each sleeve portion is provided.

7. An intermediate sleeve blank according to claim 5, wherein the metal material of the sleeve is a titanium alloy.

8. An intermediate sleeve blank according to claim 7, wherein the titanium alloy is a Ti, 3Al, 2.5V alloy.

9. A sleeve for a dental handpiece, said sleeve, in the longitudinal direction, having a shape in cross section along an outer dimension extending from a first cross section to a second different cross section, said sleeve having a wall thickness varying with different cross sections and having a greater thickness at a smaller cross section, said sleeve being a homogeneous seamless tube of a metal material suitable for super-plastic deformation.

10. A sleeve according to claim 9, wherein said first cross section and second cross section are circular cross sections of different diameters.

11. A sleeve according to claim 9, wherein said first cross section is a non-rotational symmetric shape and said second cross section is a substantially circular cross section and said sleeve includes being curved in the longitudinal direction and has a ridge extending for a portion of its length, said ridge forming ledges with curved surfaces of the sleeve.

12. A sleeve according to claim 9, wherein the material of the sleeve is a titanium alloy, preferably of the composition Ti, 3Al, 2.5 V.

* * * * *